United States Patent [19]

Varma et al.

[11] Patent Number: 5,364,884

[45] Date of Patent: Nov. 15, 1994

[54] ARGININE COMPOUNDS AS OCULAR HYPOTENSIVE AGENTS

[75] Inventors: Rajender S. Varma, The Woodlands; George C. Y. Chiou, College Station, both of Tex.

[73] Assignee: Baylor College of Medicine, Houston, Tex.

[21] Appl. No.: 7,347

[22] Filed: Jan. 21, 1993

[51] Int. Cl.$^5$ .................. A01N 37/12; A01N 37/44
[52] U.S. Cl. .................. 514/551; 514/565; 514/616; 514/621; 514/913; 560/34
[58] Field of Search .................. 560/34; 514/565, 616, 514/621, 551, 913

[56] References Cited

U.S. PATENT DOCUMENTS

| | | | |
|---|---|---|---|
| 4,515,800 | 5/1985 | Cavero et al. | 514/392 |
| 4,694,022 | 9/1987 | Gerson et al. | 514/554 |
| 4,722,933 | 2/1993 | Horn | 514/438 |
| 4,822,819 | 4/1989 | De Santis et al. | 514/530 |
| 4,822,820 | 4/1989 | De Santis et al. | 514/530 |
| 4,828,869 | 5/1989 | Muchowski | 514/408 |
| 5,182,102 | 1/1993 | De Santis, Jr. et al. | 424/78.1 |
| 5,182,258 | 1/1983 | Chiou | 514/3 |
| 5,208,256 | 5/1993 | Ueno | 514/530 |
| 5,217,997 | 6/1983 | Levere et al. | 514/565 |

FOREIGN PATENT DOCUMENTS

| | | | |
|---|---|---|---|
| 1270195 | 6/1990 | Canada . | |
| 1270195 | 6/1990 | Canada | A61K 37/02 |
| 0257887 | 3/1988 | European Pat. Off. | C61K 31/34 |
| 0291999 | 11/1988 | European Pat. Off. | C07K 7/00 |
| 338291 | 10/1989 | European Pat. Off. . | |

OTHER PUBLICATIONS

Andronik-Lion et al., "Formation of Nitric Oxide by Cytochrome P450-Catalyzed Oxidation of Aromatic Amidoximes," *Biochem. Biophys. Res. Commun.*, 185(1):452–458, 1992.

Bodor and Visor, "Formation of Adrenaline in the Iris–Ciliary Body from Adrenalone Diesters," *Exp. Eye. Res.*, 38:621–626, 1984.

Bredt and Snyder, "Isolation of Nitric Oxide Synthetase, A Calmodulin-Requiring Enzyme," *Proc. Natl. Acad. Sci. USA*, 87:682–685, 1990.

Bundgaard, "Design and Application of Prodrugs," In: "A textbook of Drug Design and Development," P. Krogsguard-Larsen and H. Bundgaard, Eds., Harvard Academic Publishers, Philadelphia, PA 1911, pp. 124–127; 152–159.

Chiou and Li, "Ocular Hypotensive Actions of Serotonin Antagonist–Ketanserin Analogs," *J. Ophthalmol.*, 8(1):11–21, 1992.

Dhaon et al., "Esterification of N-Protected α-Amino Acids with Alcohol/Carbodiimide/4-(Dimethylamino)-pyridine. Racemization of Aspartic and Blutamic Acid Derivatives," *J. Org. Chem.*, 47:1962–1965, 1982.

Feelisch et al., "Thio;-Mediated Generation of Nitric Oxide Accounts for the Vasodilator Action of Furoxans," *Biochem. Pharmacol.*, 44(6):1149–1157, 1992.

Feelisch, "The Biochemical Pathways of Nitric Oxide Formation from Nitrovasodilators: Appropriate Choice of Exogenous No Donors and Aspects of Preparation and Handling of Aqueous No Solutions," *J. Cardiovasc. Pharmacol.*, 17(Suppl. 3):S25–S32, 1991.

Gibson et al., "An Investigation of Some S-Nitrosothiols, and of Hydroxy-Arginine, on the Mouse Anococcygeus," *Br. J. Pharmacol.*, 107:715–721, 1992.

(List continued on next page.)

*Primary Examiner*—Jose G. Dees
*Assistant Examiner*—Joseph M. Conrad
*Attorney, Agent, or Firm*—Arnold White & Durkee

[57] ABSTRACT

The invention relates to arginine and arginine-like compounds and to methods employing these compounds as ocular hypotensive agents. These compounds are effective when applied topically, may be used in low concentrations and are nontoxic. Additionally, the invention includes several new arginine derivatives with varying lipophilicities particularly suited for topical administration.

12 Claims, 5 Drawing Sheets

OTHER PUBLICATIONS

Greco et al., "GH Secretion in Open-Angle Glaucoma," *Ophthalmologica, Basel,* 179:168–172, 1979.

Hannappel et al., "Amino Acid Pattern in Human Aqueous Humor of Patients with Senile Cataract and Primary Open-Angle Glaucoma," *Ophthalmic Res.,* 17:341–343, 1985.

Horio and Murad, "Solubilization of Guanylyl Cyclase from Bovine Rod Outer Segments and Effects of Lowering $Ca^{2+}$ and Nitro Compounds," *J. Biol. Chem.,* 266(6):3411–3415, 1991.

Kilbourne et al., "Arginine Antagonists for Inhibition of Systemic Hypotension Associated with Nitric Oxide Production or Endothelialderived Relaxing Factor," *Chem. Abstracts,* CA Selects: Antitumor Agents, 26:15, Abstract #115:248105v, 1991, regarding PCT application WO 9109524.

Lee, "Mechanisms and Facilitation of Corneal Drug Penetration," *J. Controlled Release,* 11:79–90, 1990.

Lee and Li, "Prodrugs for Improved Ocular Drug Delivery," *Advanced Drug Delivery Reviews,* 3:1–38, 1989.

Ludwig and Van Ooteghem, "The Evaluation of Viscous Ophthalmic Vehicles by Slit Lamp Fluorophotometry in Humans," *Int. J. Pharm.,* 54:95–102, 1989.

Moncada et al., "Nitric Oxide: Physiology, Pathophysiology, and Pharmacology," *Pharmacol. Rev.,* 43(2):109–142, 1991.

Myers, "Vasorelaxant Properties of the Endothelium-Derived Relaxing Factor More Closely Resemble S-Nitrosocysteine than Nitric Oxide," *Nature,* 345:161–162, 1990.

Nathanson, "Nitrovasodilators as a New Class of Ocular Hypotensive Agents," *J. Pharmacol. Exp. Ther.,* 260(30:956–964, 1992.

Park, "Reaction of S-Nitrosoglutathione with Sulhydryl Groups in Protein," *Biochem. Biophys. Res. Commun.,* 152(2):916–920, 1988.

Patel and Price, "Synthesis of Benzyl Esters of α-Amino Acids," *J. Org. Chem.,* 30:3575–3576, 1965.

Radomski et al., "S-Nitroso-Glutathione Inhibits Platelet Activation in *Vitro* and *in Vivo,*" *Br. J. Pharmacol.,* 107:745–749, 1992.

Robin et al., "Effects of ALO 2145 on Intraocular Pressure Following Argon Laser Trabeculoplastry," *Arch. Ophthalmol.,* 105:646–650, 1987.

Robin et al., "Effects of Topical ALO 2145 (*p*-Aminoclonidine Hydrochloride) on the Acute Intracular Pressure After Argon Laser Iridotomy," *Arch. Ophthalmol.,* 105:1208–1211, 1987.

Rubanyl et al., "Evidence That a S-Nitrosothiol, but Not Nitric Oxide, May Be Identical with Endothelium-Derived Relaxing Factor," *J. Cardiovasc. Pharmacol.,* 17(Suppl. 3):S41–S45, 1991.

Thomas and Ramwell, "Interaction of Non-Arginine Compounds with the Endothelium Derived Relaxing Factor Inhibitor, $N^G$-Monomethyl L-Arginine," *J. Pharmacol. Exp. Ther.,* 260(2):676–679, 1992.

Traylor and Sharma, "Why No?", *Biochemistry,* 31(11):2647–2648, 1992.

Venturini et al., "Synthesis of Nitric Oxide in the Bovine Retina," *Biochem. Biophys. Res. Commun.,* 180(2):920–925, 1991.

Yoshimura et al., "The Use of Arginine of Ornithine as an Immunostimulator," *Chem. Abstracts,* CA Selects:Antitumor Agents, 26:15, Abstract #115:248101r, 1991, regarding PCT application WO 9109524.

Zervas et al., "Studies on Arginine Peptides. I. Intermediates in the Synthesis of N-Terminal and C-Terminal Arginine Peptides," *J. Org. Chem.,* 22:1515–1521, 1957.

Dialog Search Report.

*Di-O-(N<sub>α</sub>-benzoyl-L-arginyl)ethylene glycol*

*Tri-O-(N<sub>α</sub>-benzoyl-L-arginyl)glycerol*

FIGURE 5

ARGININE COMPOUNDS AS OCULAR HYPOTENSIVE AGENTS

BACKGROUND OF THE INVENTION

1. Field of the Invention

The invention relates to novel arginine and arginine-like compounds, compositions for treating ocular hypertension and methods for prevention of retinal degeneration employing the compositions. The invention also includes methods for stimulating nitric oxide (NO) production and activation of guanylate cyclase.

2. Description of Related Art

Ocular hypertension is a commonly encountered condition in the human eye and is particularly associated with glaucoma. Glaucoma and many other diseases and conditions such as diabetic retinopathy, sickle cell retinopathy, hypertensive and atherosclerotic vascular diseases, retinal vein occlusion and ischemic maculophaty may significantly effect retinal circulation and nutrient supply. Such impairment may lead to degeneration of the retina and optic nerve with ultimate loss of vision. Compounds that relieve ocular hypertension thus enhancing blood flow and nutrients supplied to the retina may slow or even prevent vision loss. However, many classes of compounds have systemic side effects that may be inappropriate for the condition treated, thus making it desirable to identify new agents with actions directed mainly to reduction of ocular hypertension.

To add to the problem, some drugs when given systemically or locally applied to the eye for reasons other than reduction of ocular hypertension may cause a decrease in ocular circulation generally as a side effect. Therefore, there are significant number of instances of decreased ocular flow resulting from unrelated disease conditions.

Treatment of open angle glaucoma is a typical case in point. Average incidences of open angle glaucoma in the general population at age 40 and older is relatively high, about 2-3% (Greco et al., 1979). Numerous compositions have been reported to be of value in treating such conditions as glaucoma by decreasing intraocular pressure (IOP). These compounds include alkaloids (EPA 257887), atrial natriuretic factor (ANF), peptides (EPO 291999A2), substituted 2-aminotetralins (U.S. Pat. No. 4,722,933), phenylimino-imidazoles (U.S. Pat. No. 4,515,800), betaxolol salts (U.S. Pat. No. 4,694,022), and vasodilators such as nitroglycerine (Nathanson, 1992). These compounds are representative of some of the agents that have been tested to reduce intraocular pressure. Interestingly, arginine and arginine derivatives have been suggested as prophylaxis or treatment of an animal for systemic hypotension induced by biological response modifiers such as tumor necrosis factor, interleukin-2 or endotoxin (Kilbourne, et al., WO 91/04024).

Unfortunately, while many of the compounds studied do indeed decrease IOP, there are other often undesirable physiologic effects. Some of these classes of ocular hypotensives may also have some degree of risk associated with use due mainly to toxicity, as well as mutagenic or immunosuppressive effects.

There is thus a continued need for improved pharmaceutical compounds for treatment of ocular hypertension and glaucoma that may be administered topically or otherwise that will act effectively and selectively in reducing intraocular pressure without other pharmacological action or untoward side effects. Particularly desirable agents are those effective in low dosages and which lack toxicity.

SUMMARY OF THE INVENTION

The present invention addresses one or more of the foregoing problems encountered in controlling ocular hypertension. The invention is concerned with agents that are effective and nontoxic, identified as arginine and closely related compounds, which in the form of preparations suitable for ocular administration act to inhibit ocular hypertension. The invention also relates to novel arginine derivatives which may be metabolized in vivo to arginine and which may be tailored to provide varying lipophilicities and/or bioavailability.

The methods of the present invention relate generally to reducing intraocular pressure which involve administration of an effective amount of a pharmaceutically acceptable composition that contains arginine or an arginine like compound. By arginine like compound is meant a compound with the basic arginine structure, but which may be variously substituted at the $N_\alpha$ nitrogen of the molecule or have an ester or an amide function in place of the free carboxyl group, or both.

Preferred arginine compounds of the present invention have the L-isomer configuration and preferred compounds include L-arginine and $N_\alpha$-substituted L-arginine ester derivatives with $N_\alpha$-benzoyl-L-arginine hydrochloride particularly preferred. Carboxylate esters are equally suitable and the ester group may be selected from methyl, ethyl, isopropyl, isobutyryl, t-butyryl, valeryl, isovaleryl and benzyl moieties. Suitable $N_\alpha$-substituents include benzoyl or acetyl groups to form amide derivatives, and t-butyloxycarbonyl (Boc) and benzyloxycarbonyl (Cbz) groups to form carbamate derivatives. As an example of carbamate class derivatives, arginine-like compounds consisting essentially of $N_\alpha$-benzyloxycarbonyl derivatives of L-arginine are also suitable. Again, the carboxyl ester group may be selected from methyl, ethyl, isopropyl, t-butyl, benzyl and the like. Other suitable compounds include benzyl esters of L-arginine variously substituted at the $N_\alpha$-position. $N_\alpha$-substituents may include acetyl, benzoyl, t-butyloxycarbonyl and benzyloxycarbonyl functionalities.

Numerous other arginine compounds are considered suitable for the practice of the present invention. Considerations in selecting a suitable arginine compound will be based on the recognized difficulty of topically introducing compounds into the eye, due to factors such as absorption properties of the cornea and conjunctiva, tear turnover and solution drainage, recognizing that most ophthalmic preparations are administered as solutions. Therefore, one will desire to choose substituent groups that enhance the lipophilicity of the molecule with the objective of increasing the availability of the drug at the corneal surface and/or passage through the membrane. Likewise, one might also select "prodrug" compounds that will hydrolyze to arginine. For cleavage or hydrolysis one will wish to consider both the vehicle in which the compound is applied to the eye and also the potential of the ocular environment to cleave such compounds. For example, the aqueous humor of the eye may contain different esterases. Rabbit ocular tissues contain acetyl and butyrylcholinesterase (Lee and Li, 1989), with butyrylcholinesterase dominant, as it is in most ocular tissue. It is reported that lipophilic esters are hydrolyzed more readily than the hydrophilic esters, suggesting that hydrolysis and therefore availability may be increased by appropriate ester selection (Lee and Li, 1989). Lacrimal glands produce tears which do not generally contain esterases, although dilution and washing effects are a consideration in applying aqueous drug preparations directly to the eye.

Figure 5:
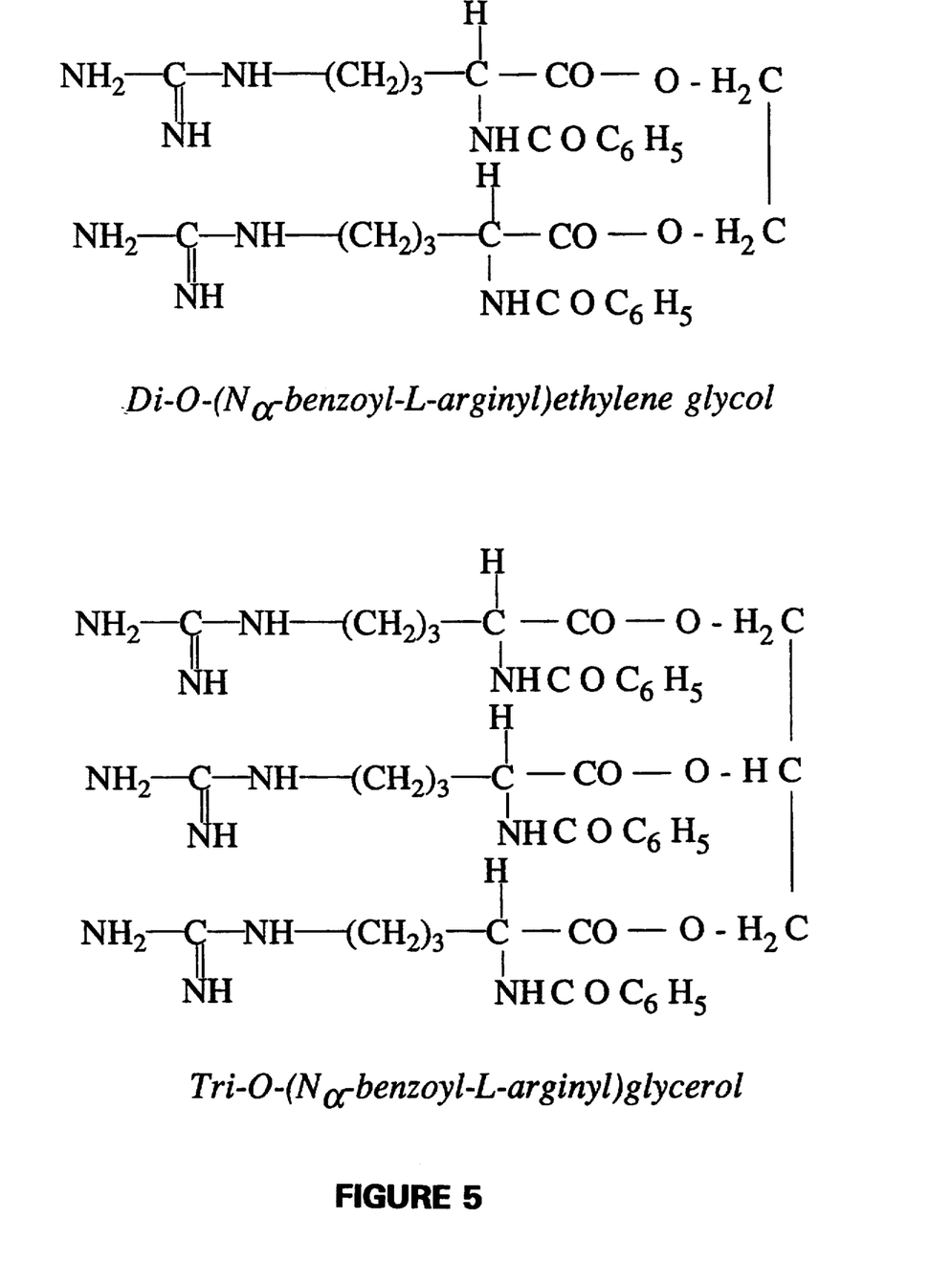
FIG. 5 shows the structures of Di-O-($N_\alpha$-benzoyl-L-arginyl)ethylene glycol and tri-O-($N_\alpha$-benzoyl-L-arginyl)glycerol.

Thus, diesters or triesters of arginine such as the trimeric shown in FIG. 5 would be expected to hydrolyze readily in the ocular environment to produce arginine. Hydrolysis rate and therefore the rate of release could be controlled to some extent by the number of arginine moieties. This would also be affected by the nature of any $N_\alpha$-substituents. Relatively large substituents, such as benzyl groups, would tend to slow hydrolysis because of steric interference, while smaller groups would likely permit faster hydrolysis. Moreover, lipophilicity of the compounds could be controlled to some extent by the nature of $N_\alpha$-substituents, thereby providing some control and variation over absorption into the eye.

Other compounds which are metabolites of arginine are also envisioned. These include $N_\alpha$-hydroxy-L-arginine derivatives and specifically $N^\omega$-hydroxy-L-arginine and its various $N_\alpha$-protected ester forms. Such $N^\omega$-hydroxyarginines substituted at the $N_\alpha$-position with acetyl, benzoyl or t-butyloxycarbonyl groups and with or without esterification of the carboxyl group are also potential candidates for reducing ocular hypertension. An example is $N_\alpha$-(t-butyloxycarbonyl)-$N^\omega$-hydroxy-L-arginine-tertbutyl ester.

Appropriate compounds for the practice of the present invention need not be limited to L-arginine and arginine derivatives. It is known that nitric oxide synthase converts L-arginine to NO (Bredt and Snyder, 1990). NO is involved in several important biological events including vascular smooth muscle relaxation, platelet deaggregation, neuronal communication and possible photoreceptor signaling, to mention a few. NO involvement occurs through activation of guanylate cyclase, which is a heme containing enzyme catalyzing the reaction GTP→cGMP. Vasodilators such as nitroglycerin exert their pharmacological action by releasing nitric oxide. Thus, compounds that, like L-arginine, release NO in the presence of nitric oxide synthase will be expected to act like L-arginine as effective reducers of ocular hypertension. Generally, such compounds would contain amidine or amidoxime functions which could act as precursors of NO in vivo after oxidation by suitable enzymes in the presence of oxygen and NADPH. Aryl amidoximes would be particularly useful because of their increased lipophilic character.

Nitrosothiols are another class of useful compounds that may stabilize highly reactive and unstable NO by increasing its half-life in vivo. It has been suggested (Myers, et al., 1990) that endothelium-derived relaxing factor (EDRF) may be a nitrosothiol, possibly identical to S-nitrosocysteine. S-nitroso-glutathione is a relatively stable S-nitrosothiol that is easily obtainable from abundant intracellular thiols. Glutathione, therefore, may be particularly useful in stabilizing NO (Radomski, et al., 1992).

Other aspects of the present invention include methods of preventing ischemic retinal degeneration. This refers to the protection of the retina by increasing blood flow or nutrients to the retina. This may be accomplished through vasodilatation or increasing permeability of the blood vessels which are both attributes of NO. The low toxicity of the arginine compounds disclosed herein for reduction of intraocular pressure, makes them particularly suitable for prophylactic administration. Thus, individuals with a tendency to develop ocular hypertension either through genetic predisposition or age, such as subjects with acute- or open-angle glaucoma, could be treated with such compounds. Other uses would be to counteract the effect of unrelated medications or surgical procedures which have a side effect of increasing intraocular pressure. In such cases, administration of the arginine compounds would be a simple and effective means of preventing retinal degeneration.

Administration of arginine or arginine-like compounds would be in the form of a pharmaceutically acceptable composition, several aspects of which will now be discussed.

Ophthalmic compositions intended to be administered topically will have a pH range from about 3 to about 9.5 and most preferably around pH 7.0–7.5 in order to avoid tissue irritation or damage. Any of numerous suitable non-toxic buffering agents may be employed including acetate, borate, carbonate, phosphate, citrate, Tris, etc. Compositions suitable for ocular administration are preferably in the form of emulsions, solutions, gels, aerosols or ointments. The preparation of such an ophthalmic composition would be generally known to those of skill in the art, as described, for example, in "Remington's Pharmaceutical Sciences" 15th Edition (Mack Publishing Co., Easton, Pa.).

Ointment bases typically are formulated as white or yellow ointments with cetyl ester waxes, oleic acid, paraffin, petrolatum, hydrophilic petrolatum or white petrolatum. Other ointment components may include mineral oil, lanolin, anhydrous lanolin, glycerol monosteate or cetyl alcohol. Water soluble ointment bases and components may incorporate glycol ethers and their derivatives, polyethylene glycols, polyoxyl 40 stearate and polysorbates.

In general one will wish to employ a suitable ophthalmic carrier in sterile, substantially isotonic aqueous solutions. Such solutions will typically maintain sterility by employing well-known ophthalmic preservatives; for example thimerosal, cetylpyridinium chloride, benzalkonium chloride, phenylmercuric salts, etc. The amount of these preservatives employed is generally about 0.001 to 0.1% by weight. Particularly suitable preservatives for ointments include methyl and propyl parabens.

Conventional carriers as well as those particularly suited for ophthalmic applications may be employed in the present invention. As examples, carriers may consist of sterile ophthalmic ointments, cream gels, or various solutions or dispersions. For some applications slow release formulations may be particularly preferred. Suitable slow release polymers may be formulated from dextrose, dextran, polylactic acid, and various cellulose derivatives, for example ethylhydroxycellulose in the form of microcapsules.

Further examples of suitable carriers, excipients and diluents include lactose, dextrose, sucrose, sorbitol, mannitol, starches, gum acacia, calcium phosphate, alginates, calcium silicate, microcrystalline cellulose, polyvinyl pyrrolidine, cellulose, tragacanth, gelatin syrup, methylcellulose, methyl and propyl hydroxybenzoates, talc, magnesium stearate, water and mineral oil. Other additives optionally include lubricating agents, wetting agents, emulsifying and suspending agents or preserving agents. Compositions may be formulated to provide immediate, sustained or delayed release of the compound.

Various additives may be added to the formulation including substances which serve for emulsification, preservation, wetting, improving consistency and so forth and which are conventionally employed in pharmaceutical preparations. Other additives may also be used. These include compounds that have surfactant properties, either ionic or non-ionic such as sorbitan monolaurate triethanolamine oleate, polyoxyethylenesorbitan monopalmitate, dioctyl sodium sulfosuccinate, monothioglycerol, thiosorbitol, ethylenediamine tetra-acetic acid, etc.

Suitable preservatives for use in the pharmaceutical preparations include benzalkonium chloride, benzethonium, phenylethyl alcohol, chlorobutanol, thimerosal and the like. Suitable buffers include boric acid, sodium and potassium bicarbonate, sodium and potassium borates, sodium and potassium carbonate, sodium acetate, sodium biphosphate, and the like, in amounts sufficient to maintain the pH between about pH 3 and about pH 9.5, most preferably between about pH 7 and pH 7.5. Suitable tonicity agents are dextran 40, dextran 70, dextrose, glycerin, potassium chloride, propylene glycol, sodium chloride and the like, such that the sodium chloride equivalent of the ophthalmic solution is in the range of 9.9±0.2%.

Suitable antioxidant and stabilizers include sodium and potassium bisulfite, sodium and potassium metabisulfite, sodium thiosulfate, thiourea and the like. Suitable wetting and clarifying agents include polysorbate 80, polysorbate 20, poloxamer 282 and tyloxapol. Suitable viscosity increasing agents include dextran 40, gelatin, glycerin, hydroxyethyl cellulose, hydroxymethyl propyl cellulose, lanolin, methylcellulose, petrolatum, polyethylene glycol, polyvinyl alchohol, polyvinyl polyvinylpyrrolidone, carboxymethyl cellulose and the like.

Stabilizers such as chelating agents, for example EDTA, EGTA, DTPA, DOTA, ethylene diamine, bipyridine, 1,10-phenanthrolene, crown ethers, aza crown, catechols, dimercaprol, D-penicillamine and deferoxamine may be used. Antioxidants will also act as stabilizers and include such compounds as ascorbic acid, sodium bisulfite, ascorbyl palmitate, butylated hydroxyanisole, butylated hydroxytoluene, potassium metabisulfite and sodium metabisulfite.

Viscosity agents are often added to prevent extensive drug loss by drainage once an aqueous preparation is instilled in the eye. Several compounds are suitable for this purpose, including methylcellulose, hydroxypropylmethylcellulose, polyvinyl alcohol, dextran, and hydroxyethylcellulose (Ludwig and Van Ooteghem, 1989).

In addition to administration in liquid or ointment form, solid inserts for use in the eye may be employed. Such an insert will be in a form suitable for insertion into the area of the eye known as the cul de sac (a pocket-like area formed with the conjunctiva). The insert, which is combined with one or more active ingredients may be biodegradable or non-biodegradable. Considerations in the choice of biodegradable material would include the effect of tears or lacrimal fluids on the material particularly with regard to the normal pH of tears which is 7.2.

Liposomal preparations are contemplated to be a particularly useful form of application for the arginine compounds. One would incorporate arginine compounds into various liposomes by mixing with the appropriate lipids or phospholipids. Some arginine compounds, for example the tri-($N_\alpha$-benzoyl-L-argininyl)-glycerol species, may themselves spontaneously form vesicles under proper conditions, thus providing a form of the compound with altered release and/or metabolic rates.

As used herein a therapeutically effective amount is an amount which upon single or multiple dose administration produces a desired therapeutic effect by significantly altering intraocular pressure to cause changes to more normal values.

Typically used doses will generally be in the range of about 0.01% to 5% by weight, and usually about 0.1–0.5% when used topically. Frequency of treatment and dose level will, however, depend upon the severity of the condition and the nature of the disease being treated. Generally speaking, and in the cases of, for example, glaucoma, treatment will typically be from 3 to 4 times daily by topical administration.

Pharmaceutically acceptable compositions of arginine or arginine-related compounds may be applied topically to the ocular surface either alone or in combination with other drug delivery systems. Examples of such systems include hyaluronic acid solutions or suspensions of collagen fragments. The drugs may be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide] and the like. Particular formations may be in the form of liquid suspensions, ointments, complexes to a bandage, collagen shield or the like. In some cases, for example where there is existing damage to the cornea, the compositions may be administered intradermally or possibly subcutaneously.

The invention is therefore directed to compositions which include one or more arginine or arginine-related compounds in suitable pharmaceutical compositions that include pharmaceutically acceptable carriers. Ophthalmic solutions for topical administration for example would be administered to the eye of the subject in need of treatment in the form of an ophthalmic preparation prepared in accordance with conventional pharmaceutical practice, see for example Remington's Pharmaceutical Sciences, 15th Ed., pp. 1488–1501, Mac Publishing Co., Easton, Pa.

Conditions amenable to treatment with the disclosed methods are not limited to glaucoma, but also extend to any condition where ocular hypertension exists or it is desirable to prevent ocular hypertension.

DETAILED DESCRIPTION OF PREFERRED EMBODIMENTS

The enzyme nitric oxide synthase converts L-arginine to nitric oxide (NO) (Bredt and Snyder, 1990). The endogenously produced nitric oxide is also known as endothelium derived relaxation factor (EDRF) and has been implicated in the role of relaxing vascular smooth muscles. It is a potent stimulator of guanylate cyclase in several systems including retina (Venturini et al., 1991). Recently, however, it has been suggested that S-nitrosothiols, but not free NO, are identical to EDRF rather than NO (Rubanyi et al., 1991). Additionally, the role of NO in physiological function is beginning to be elucidated, for example its role in vasodilation and platelet aggregation when combined with intracellular thiols (Radomski, et al., 1992; Myers, et al., 1990).

There is evidence of the presence of NO synthase in bovine retina (Venturini et al., 1991), activation of bovine rod outer segment guanylate cyclase by NO and the role of exogenous lipophilic activators or soluble guanylate cyclase in altering intraocular pressure. Thus, the discovery of L-arginine as a substrate for NO synthase prompted in vivo testing of this compound for reducing intraocular pressure. Surprisingly, the topical use of L-arginine and its lipophilic derivatives which are also substrates for the NO synthase, provide a convenient source of NO. NO is a potent vasodilator and modulator of guanylate cyclase thus making it an ideal compound for lowering intraocular pressure and for preventing and controlling retinal degeneration. L-arginine is a widely occurring, non-toxic natural amino acid.

Arginine and some of its lipophilic derivatives have been tested in animal models. Data are provided in the following examples for L-arginine, N-α-benzoyl-L-arginine ethyl ester hydrochloride, L-homoarginine hydrochloride, and L-(+)-canavanine sulfate monohydrate. In general, L-arginine and L-arginine analogs show an effect on intraocular pressure (IOP), as clearly demonstrated in the recovery curve of rabbits infused with hypertonic saline. Several compounds showed a marked delay in IOP recovery, indicating their potential as ocular hypotensive agents. The compounds showed equal suppression of the IOP recovery curves of treated and contralateral eyes indicating a systemic effect but not necessarily excluding local effects.

Methods

Testing of the disclosed compounds was performed in a rabbit model. The general procedure is described below. Results for specific compounds are illustrated in the examples.

New Zealand white rabbits weighing 2.5–3.0 kg were used for the experiments. Rabbits were tested twice: the first time for controls and the second time, one week later, for treated. For controls, rabbits were infused with 20% saline solution at 1 ml/min for 10 min through the ear vein. The IOP was measured with an electronic applanation tonometer (Alcon, Fort Worth, Tex.) after 1 drop of proparacaine as a local anesthetic. The IOP was measured at $t = -10, 0, 10, 20, 40, 60$, and 80 minutes, and every 30 minutes thereafter. The IOP measured at $-10$ min was considered as 100% response. The IOP dropped precipitously in the first 10 min. where the hypertonic saline was infused, and recovered gradually over a 70–100 minute period. One week later, the rabbits were tested again in the same manner as the first week except that the right eye received the drug solution as "treated" and the left eye received the vehicle as "contralateral non-treated". The drug solution or vehicle was given at $-30$ min., and the IOP measure at this time was considered as 100% response. The rest of the time periods when the IOP was measured were the same as in the first week.

When the IOP recovery time of the treated curve is prolonged, or the slope of the IOP recovery curve is suppressed by an agent, it indicates that this agent may produce an antiglaucoma action. An equal degree of suppression of IOP recovery curve at treated and contralateral non-treated eyes indicates that the drug may produce its ocular hypotensive action on the contralateral eye through a systemic action. If the IOP recovery curve was suppressed significantly more on the treated eye than on the contralateral eye, it indicates that the drug may act primarily locally in the treated eye.

A student's t-test was used for comparing the two values, and the data were expressed as mean ±SEM. The values were considered significantly different if the P value was less than 0.05.

The following examples are included to demonstrate with more particularity the techniques and methodology employed by the present inventors to utilize the novel arginine and arginine-like compounds disclosed herein for reducing hyperocular pressure. It should be appreciated that these examples are exemplary only and that a variety of possible ways of achieving the same end will be apparent to those of skill in the art in light of the following disclosure. For example, the method could be practiced with numerous arginine related compounds, synthesized to have varying degrees of lipophilicity depending on the absorption characteristics desired. All such modifications are intended to be within the spirit and scope of the invention.

EXAMPLE 1

This example illustrates the effectiveness of L-arginine in delaying intraocular pressure recovery in rabbit models where intraocular pressure has been reduced. An aqueous solution of L-arginine was tested in the eyes of rabbits and showed a significant effect in delaying IOP increase.

Reduction of Intraocular Pressure in the Rabbit

Arginine was prepared as a 5 mg/ml aqueous solution in phosphate buffered saline (PBS). 50 μl was administered to the right eye at the times indicated in the general procedure described under Methods. The intraocular pressure was measured at $-30, -10, 0, 10, 20, 40, 60$ and 80 minutes and every 30 minutes thereafter. PBS alone was administered to the left eye. Control measurements were obtained, as detailed previously, by administering PBS one week prior to the measurements made with the arginine solutions.

Control values showing the changes in intraocular pressure from administration of a 20% saline solution (hypertonic) via the ear vein are shown in Table 1. One week later, the same animals were tested by administering a 0.5% solution of L-arginine in PBS to the right eye and a PBS solution to the left eye. Changes in intraocular pressure over a period of 260 min are tabulated in Table 2. There was a distinct prolongation of recovery time for intraocular pressure in both eyes, indicating a systemic effect.

Figure 1:
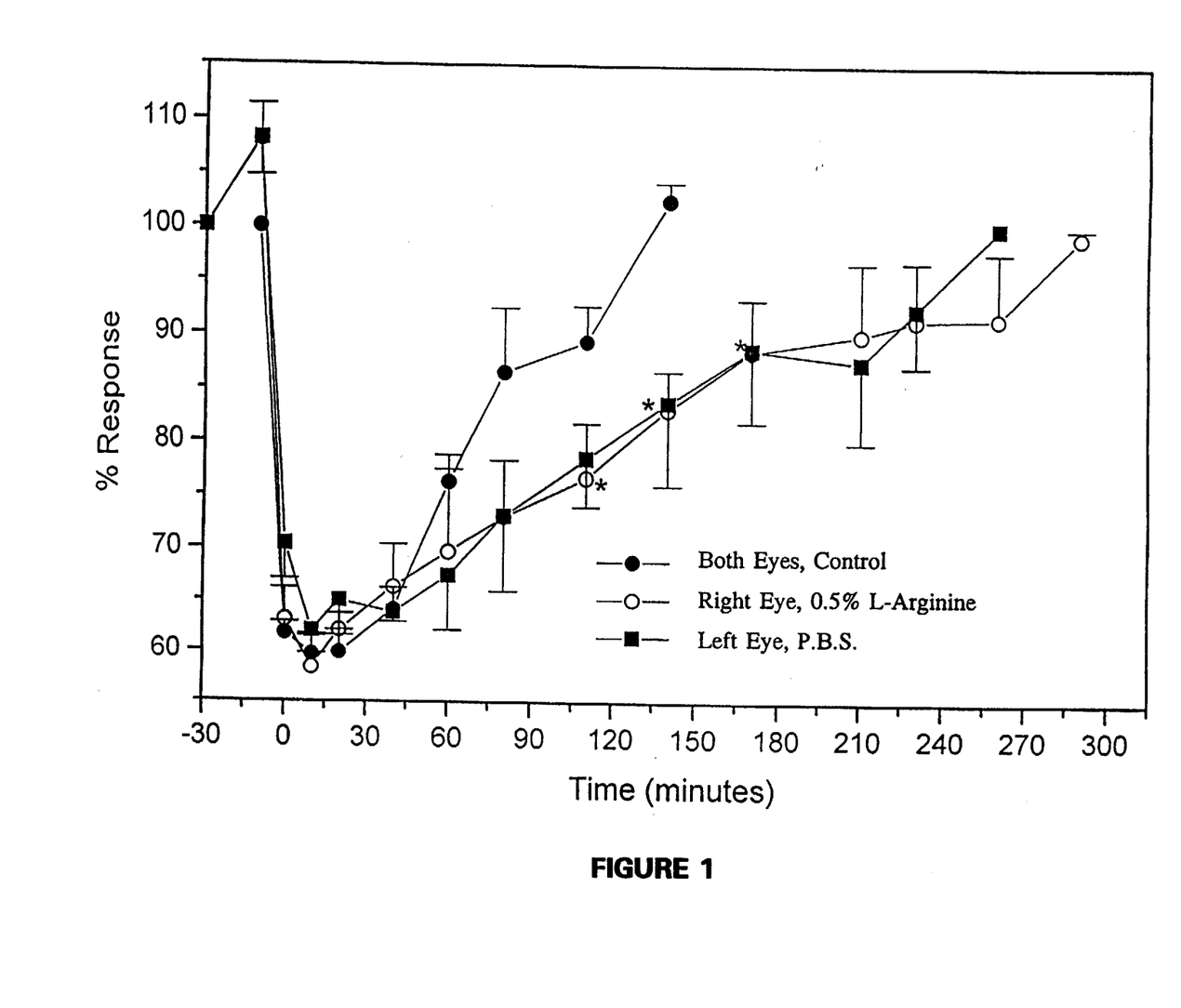
FIG. 1 is a graphical representation of the data of Tables 1 and 2, indicating response of intraocular pressure over time to administration of an aqueous solution of a 0.5% aqueous solution of L-arginine applied to the right eye of a rabbit. Error bars are indicated for each measurement which represents combined results from four rabbits.

The results are summarized in FIG. 1.

TABLE 1

| ANIMAL | −10 | 0 | 10 | 20 | 40 | 60 | 80 | 110 | 140 | 170 | 200 |
|---|---|---|---|---|---|---|---|---|---|---|---|
| | | | | | | Control | | | | | |
| | | | | | Right Eye | | | | | | |
| 3232 | 100 | 59.3 | 53.1 | 53.1 | 56.2 | 75.0 | 68.8 | 81.3 | 100 | | |
| 3233 | 100 | 58.3 | 62.5 | 70.8 | 66.7 | 75.0 | 79.2 | 100 | 108.3 | | |
| 3234 | 100 | 64.0 | 60.0 | 60.0 | 64.0 | 72.0 | 84.0 | 80.0 | 100 | | |
| 3235 | 100 | 66.7 | 58.3 | 62.5 | 66.7 | 87.5 | 116.7 | 100 | | | |
| | | | | | Left Eye | | | | | | |
| 3232 | 100 | 59.3 | 53.1 | 50.0 | 56.2 | 65.6 | 75.0 | 81.3 | 100 | | |
| 3233 | 100 | 60.0 | 68.0 | 60.0 | 64.0 | 80.0 | 84.0 | 92.0 | 112 | | |
| 3234 | 100 | 64.0 | 64.0 | 60.0 | 64.0 | 72.0 | 76.0 | 80.0 | 100 | | |
| 3235 | 100 | 62.3 | 58.3 | 62.5 | 75.0 | 83.3 | 108.3 | | | | |
| | | | | | Both Eyes | | | | | | |
| Mean of Both Eyes | | 61.8 | 59.7 | 59.9 | 64.1 | 76.3 | 80.5 | 89.3 | 102.5 | | |
| SD | | 3.0 | 5.2 | 6.3 | 6.1 | 7.0 | 16.9 | 9.6 | 7.4 | | |
| SE | | 1.1 | 1.8 | 3.2 | 3.1 | 2.5 | 6.0 | 3.4 | 1.7 | | |

TABLE 2

| ANIMAL | −30 | −10 | 0 | 10 | 20 | 40 | 60 | 80 | 110 | 140 | 170 | 210 | 230 | 260 | 290 |
|---|---|---|---|---|---|---|---|---|---|---|---|---|---|---|---|
| | | | | | | | Right Eye 0.5% L-Arginine | | | | | | | | |
| 3232 | 100 | 106.5 | 58.1 | 54.8 | 58.1 | 61.3 | 64.5 | 61.3 | 64.5 | 74.2 | 80.6 | 87.1 | 77.4 | 74.2 | 96.8 |
| 3233 | 100 | 103.8 | 61.5 | 53.8 | 65.2 | 61.5 | 61.5 | 76.9 | 76.9 | 80.8 | 100 | 100 | 100 | 100 | 100 |
| 3234 | 100 | 104 | 72.0 | 68.0 | 64.0 | 64.0 | 60.0 | 68.0 | 76.0 | 88.0 | 80.0 | 72.0 | 88.0 | 92.0 | 100 |
| 3235 | 100 | 117.9 | 60.7 | 57.1 | 60.7 | 78.5 | 92.9 | 85.7 | 89.3 | 89.3 | 92.9 | 100 | 100 | 100 | 100 |
| Mean | 100 | 108.1 | 63.1 | 58.4 | 62.1 | 66.3 | 64.7 | 73.0 | 76.7 | 83.1 | 88.4 | 90.0 | 91.4 | 91.6 | 99.2 |
| SD | 0 | 6.7 | 6.1 | 6.5 | 3.3 | 8.2 | 15.6 | 10.6 | 10.1 | 7.0 | 9.8 | 13.3 | 10.9 | 12.2 | 1.6 |
| SB | 0 | 3.3 | 3.1 | 3.3 | 1.6 | 4.1 | 7.8 | 5.3 | 5.1 | 3.5 | 6.9 | 6.7 | 5.4 | 6.1 | 0.8 |
| | | | | | | | Left Eye P.B.S. | | | | | | | | |
| 3232 | 100 | 103.2 | 61.3 | 61.3 | 58.1 | 61.3 | 58.1 | 58.1 | 67.7 | 61.3 | 74.2 | 77.4 | 77.4 | 100 | 100 |
| 3233 | 100 | 107.7 | 76.9 | 61.5 | 73.1 | 65.4 | 61.5 | 80.8 | 80.8 | 96.2 | 100 | 100 | 100 | 100 | |
| 3234 | 100 | 104 | 72.0 | 68.0 | 68.0 | 64.0 | 68.0 | 64.0 | 76.0 | 88.0 | 80.0 | 72.0 | 92.0 | 100 | 100 |
| 3235 | 100 | 117.9 | 71.4 | 57.1 | 60.7 | 64.3 | 82.1 | 89.3 | 89.3 | 89.3 | 100 | 100 | 100 | 100 | |
| Mean | 100 | 108.2 | 70.4 | 62.0 | 65.0 | 63.8 | 67.4 | 73.1 | 78.5 | 83.7 | 88.6 | 87.4 | 90.4 | 100 | |
| SD | 0 | 6.8 | 6.5 | 4.5 | 6.8 | 1.7 | 10.6 | 14.4 | 9.01 | 15.4 | 13.4 | 14.8 | 10.7 | | |
| SE | 0 | 3.4 | 3.3 | 2.2 | 3.4 | 0.9 | 5.3 | 7.2 | 4.5 | 7.7 | 5.7 | 7.4 | 5.3 | | |

EXAMPLE 2

Testing of $N_\alpha$-benzoyl-L-arginine ethyl ester hydrochloride was performed as described in Example 1 for arginine. Results are shown in Tables 3 and 4 and were similar to results obtained with L-arginine.

Figure 2:
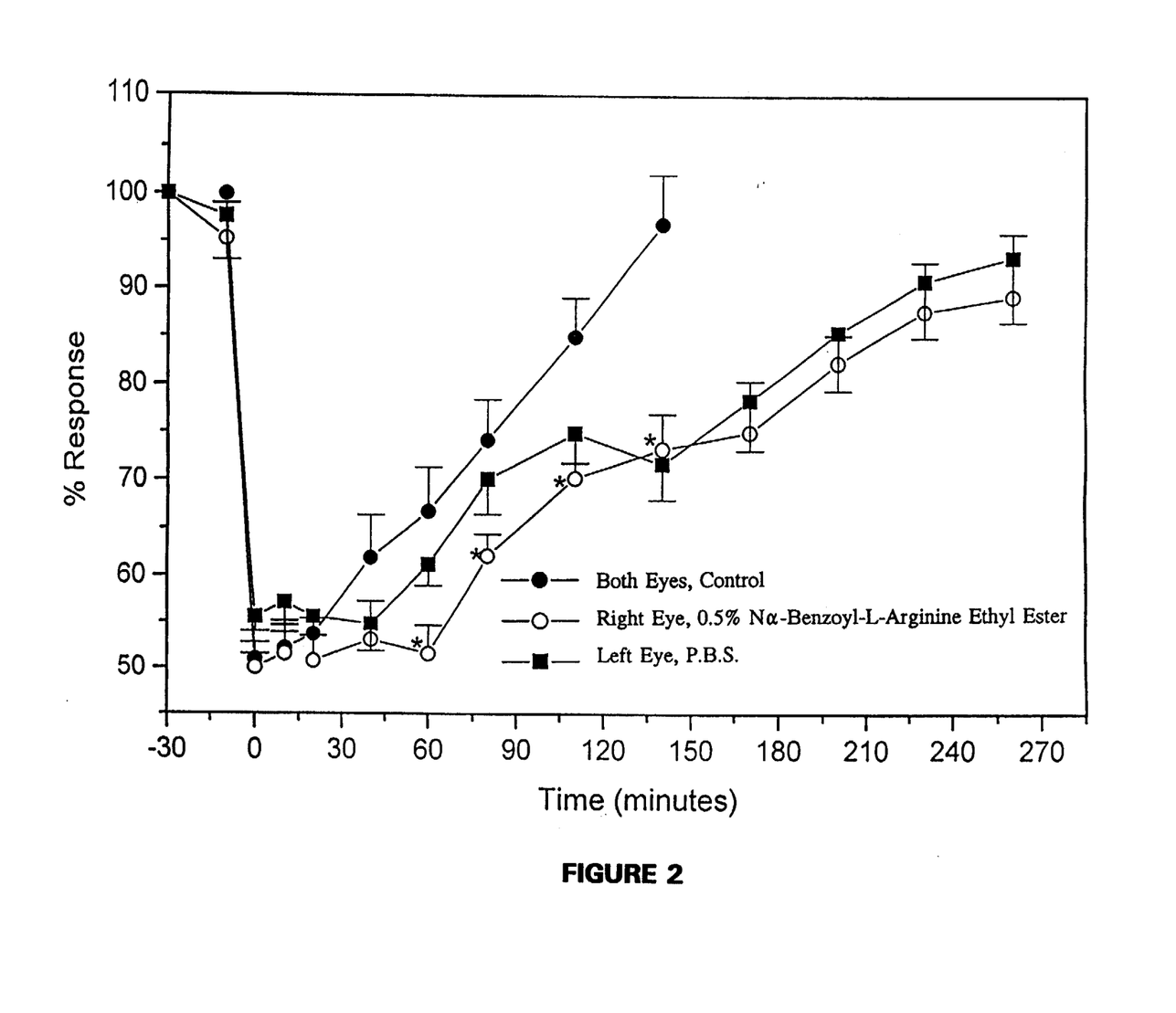
FIG. 2 is a graphical representation of the data of Tables 3 and 4, indicating response of intraocular pressure over time after administration of an aqueous solution of a 0.5% solution of $N_\alpha$-benzoyl-L-arginine ethyl ester to the right eye of a rabbit. Error bars are indicated for each measurement which represents combined results from four rabbits.

FIG. 2 is a graph representing the results tabulated in Tables 3 and 4. The data indicate that the ester, like L-arginine itself, acts systemically.

TABLE 3

| ANIMAL | −10 | 0 | 10 | 20 | 40 | 60 | 80 | 110 | 140 | 170 | 200 |
|---|---|---|---|---|---|---|---|---|---|---|---|
| | | | | | | Control | | | | | |
| | | | | | Right Eye | | | | | | |
| 3232 | 100 | 50 | 46.4 | 57.1 | 78.5 | 92.9 | 100 | 100 | 100 | | |
| 3233 | 100 | 57.1 | 64.3 | 57.1 | 57.1 | 60.7 | 67.9 | 82.1 | 100 | | |
| 3234 | 100 | 50 | 53.6 | 57.1 | 53.6 | 64.3 | 64.3 | 78.5 | 110.7 | | |
| 3235 | 100 | 46.9 | 50 | 46.9 | 56.2 | 56.2 | 68.8 | 71.9 | 75 | 87.5 | 100 |
| Mean | 100 | 51.0 | 53.6 | 54.6 | 61.4 | 68.5 | 75.3 | 83.1 | 96.4 | | |
| SE | 0 | 2.2 | 3.9 | 2.6 | 5.8 | 8.3 | 8.3 | 6.0 | 7.6 | | |
| SD | 0 | 4.3 | 7.7 | 5.1 | 11.5 | 16.6 | 16.6 | 12 | 15.1 | | |
| | | | | | Left Eye | | | | | | |
| 3232 | 100 | 46.4 | 46.4 | 57.1 | 85.7 | 78.5 | 82.1 | 100 | 100 | | |
| 3233 | 100 | 60.7 | 53.1 | 57.1 | 57.1 | 64.3 | 71.4 | 96.4 | 100 | | |
| 3234 | 100 | 50 | 50 | 50 | 53.6 | 64.3 | 64.3 | 78.5 | 114.3 | | |
| 3235 | 100 | 46.9 | 50 | 46.9 | 53.1 | 53.1 | 75 | 71.9 | 75 | 87.5 | 100 |
| Mean | 100 | 51.0 | 0.96 | 52.8 | 62.4 | 65.1 | 73.2 | 86.7 | 97.3 | | |
| SE | 0 | 3.3 | 2.2 | 3.6 | 7.8 | 5.2 | 3.7 | 6.8 | 8.2 | | |
| SD | 0 | 6.7 | 4.5 | 5.2 | 15.7 | 10.4 | 7.4 | 13.6 | 16.3 | | |

TABLE 3-continued

| | −10 | 0 | 10 | 20 | 40 | 60 | 80 | 110 | 140 | 170 | 200 |
|---|---|---|---|---|---|---|---|---|---|---|---|
| | | | | Both Eyes | | | | | | | |
| Mean | | 51.0 | 52.2 | 53.7 | 61.9 | 66.8 | 74.2 | 84.9 | 96.9 | | |
| SE | | 1.8 | 3.0 | 1.7 | 4.5 | 4.6 | 4.2 | 4.2 | 5.2 | | |
| SD | | 5.2 | 6.0 | 4.8 | 12.7 | 13.0 | 13.0 | 12.0 | 14.6 | | |

TABLE 4

| ANIMAL | −30 | −10 | 0 | 10 | 20 | 40 | 60 | 80 | 110 | 140 | 170 | 200 | 230 | 260 |
|---|---|---|---|---|---|---|---|---|---|---|---|---|---|---|
| | | | | | | | Right Eye | | | | | | | |
| | | | | | | 0.5% N-Benzoyl L-Arginine Ethyl Ester | | | | | | | | |
| 3232 | 100 | 84.4 | 46.3 | 56.2 | 50.0 | 62.5 | 59.3 | 62.5 | 68.8 | 75.0 | 68.8 | 78.1 | 96.9 | 96.9 |
| 3233 | 100 | 100 | 51.6 | 51.6 | 58.1 | 54.8 | 48.4 | 67.7 | 74.2 | 80.6 | 80.6 | 87.1 | 87.1 | 83.9 |
| 3234 | 100 | 96.8 | 48.4 | 45.2 | 45.2 | 41.9 | 45.2 | 61.3 | 71.0 | 74.27 | 87.1 | 87.1 | 93.5 | 103.2 |
| 3235 | 100 | 100 | 53.3 | 53.3 | 50.0 | 53.3 | 53.3 | 56.7 | 66.7 | 63.3 | 63.3 | 76.7 | 73.3 | 73.3 |
| Mean | 100 | 95.3 | 50.1 | 51.6 | 50.8 | 53.1 | 51.6 | 62.1 | 70.2 | 73.3 | 75.0 | 82.3 | 87.7 | 89.3 |
| SE | 0 | 3.7 | 1.5 | 2.3 | 2.7 | 4.2 | 3.1 | 2.3 | 1.6 | 3.6 | 5.4 | 2.8 | 5.2 | 6.7 |
| SD | 0 | 7.4 | 2.9 | 4.7 | 5.4 | 8.5 | 6.1 | 4.5 | 3.2 | 7.2 | 10.8 | 5.6 | 10.4 | 13.4 |
| | | | | | | | Left Eye | | | | | | | |
| | | | | | | | P.B.S. | | | | | | | |
| 3232 | 100 | 84.4 | 59.3 | 56.2 | 59.3 | 62.5 | 65.6 | 71.9 | 75.0 | 68.8 | 68.8 | 78.1 | 96.9 | 96.9 |
| 3233 | 100 | 100 | 54.8 | 54.8 | 58.1 | 54.8 | 58.1 | 71.0 | 80.6 | 80.6 | 87.1 | 90.3 | 93.5 | 100 |
| 3234 | 100 | 106.5 | 51.6 | 64.5 | 54.8 | 48.4 | 64.5 | 77.4 | 77.4 | 74.27 | 87.1 | 100 | 100 | 103.2 |
| 3235 | 100 | 100 | 56.7 | 53.3 | 50.0 | 53.3 | 56.7 | 60.0 | 66.7 | 63.3 | 70.0 | 73.3 | 73.3 | 73.3 |
| Mean | 100 | 97.7 | 55.6 | 57.2 | 55.6 | 54.8 | 61.2 | 70.1 | 74.9 | 71.7 | 78.3 | 85.4 | 90.9 | 93.4 |
| SE | 0 | 4.7 | 1.6 | 2.5 | 2.1 | 2.9 | 2.2 | 3.6 | 3.0 | 3.7 | 5.1 | 6.0 | 6.0 | 6.8 |
| SD | 0 | 9.3 | 3.2 | 5.0 | 4.2 | 5.8 | 4.5 | 7.3 | 5.9 | 7.4 | 10.2 | 12.1 | 12.0 | 13.6 |

EXAMPLE 3

Figure 3:
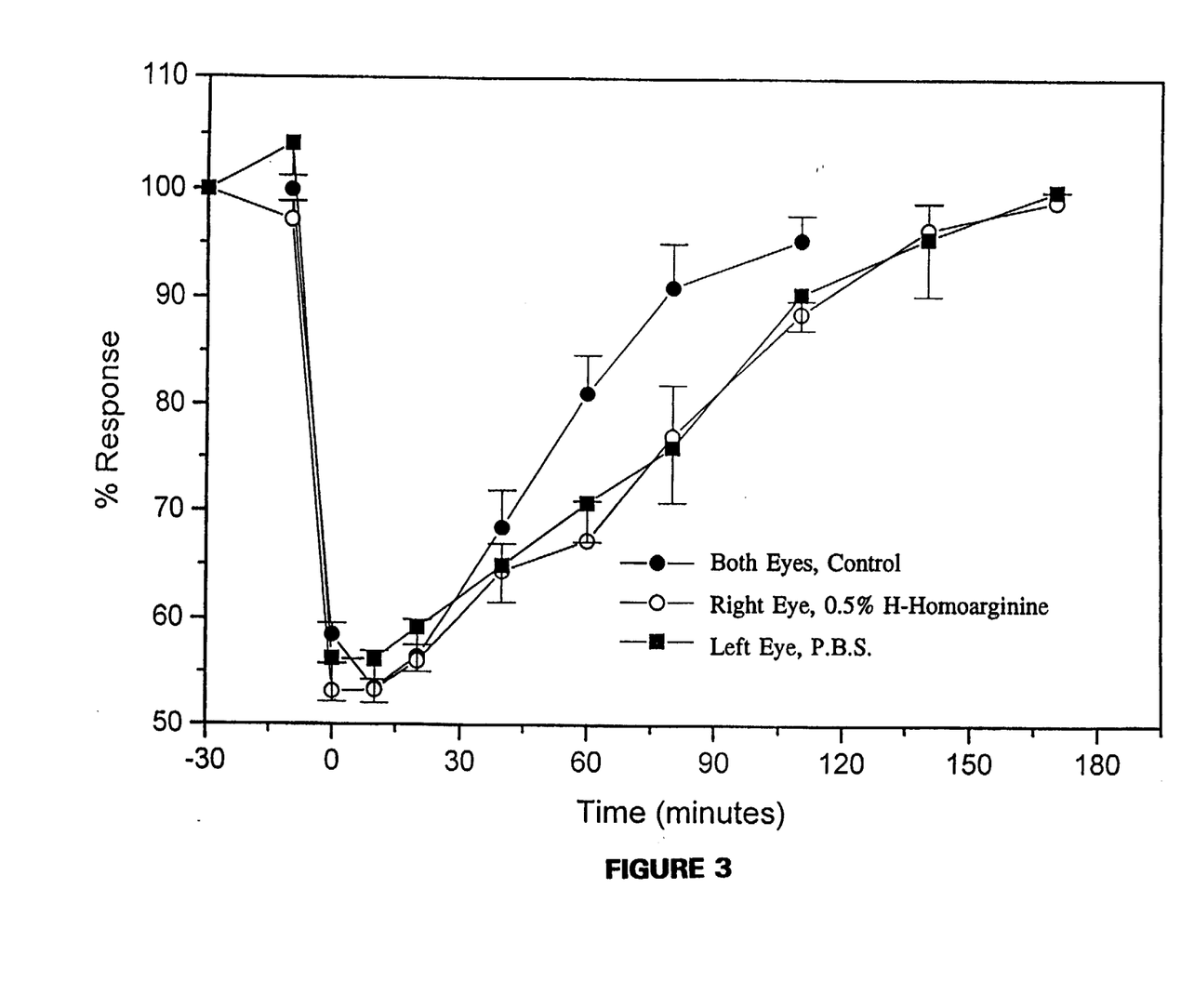
FIG. 3 is a graphical representation of the data of Tables 5 and 6, indicating response of intraocular pressure over time after administration of a 0.5% aqueous solution of L-homoarginine hydrochloride to the right eye of a rabbit. Error bars are indicated for each measurement representing combined results from four rabbits.

In contrast to arginine, L-homoarginine was ineffective in preventing intraocular pressure recovery after PBS administration in the rabbit. Tests with this compound were performed in accordance with the procedure described in Methods and in Example 1. As shown in FIG. 3, there was little difference in recovery time between control animals and animals treated with a 0.5% PBS solution of L-homoarginine. Data used to construct the graph shown in FIG. 3 are shown in Tables 5 and 6.

TABLE 5

| | −10 | 0 | 10 | 20 | 40 | 60 | 80 | 120 | 140 |
|---|---|---|---|---|---|---|---|---|---|
| AMIMAL | | | | | | | Control | | |
| | | | | Right Eye | | | | | |
| 3503 | 100 | 60.0 | 56.0 | 52.0 | 60.0 | 80.0 | 96.0 | 100 | 100 |
| 3504 | 100 | 56.0 | 52.0 | 56.0 | 60.0 | 72.0 | 88.0 | 92.0 | 100 |
| 3505 | 100 | 60.0 | 52.0 | 60.0 | 76.0 | 88.0 | 80.0 | 96.0 | 100 |
| 3506 | 100 | 60.9 | 52.2 | 56.5 | 73.9 | 87.0 | 104.3 | 100 | 100 |
| | | | | Left Eye | | | | | |
| 3503 | 100 | 60.0 | 56.0 | 56.0 | 64.0 | 76.0 | 92.0 | 100 | 100 |
| 3504 | 100 | 54.2 | 54.2 | 54.2 | 58.3 | 66.7 | 88.3 | 87.5 | 100 |
| 3505 | 100 | 56.0 | 56.0 | 60.0 | 80.0 | 92.0 | 80.0 | 88.0 | 100 |
| 3506 | 100 | 60.9 | 52.2 | 56.5 | 73.9 | 87.0 | 104.3 | 100 | 100 |
| | | | | Both Eyes | | | | | |
| Mean | 100 | 58.5 | 53.8 | 56.4 | 68.3 | 81.1 | 91.0 | 95.4 | 100 |
| SD | 0 | 2.7 | 1.9 | 2.7 | 8.6 | 8.9 | 9.9 | 5.5 | 0 |
| SE | 0 | 1.1 | 0.8 | 1.1 | 3.5 | 3.6 | 4.1 | 2.3 | 0 |

TABLE 6

| ANIMAL | −30 | −10 | 0 | 10 | 20 | 40 | 60 | 80 | 110 | 140 | 170 |
|---|---|---|---|---|---|---|---|---|---|---|---|
| | | | | | Right Eye | | | | | | |
| | | | | 0.5% L-Homoarginine Hydrochloride | | | | | | | |
| 3503 | 100 | 100 | 51.9 | 48.1 | 48.1 | 70.4 | 77.8 | 85.2 | 88.9 | 96.3 | 100 |
| 3504 | 100 | 96.0 | 56.0 | 56.0 | 56.0 | 60.0 | 64.0 | 84.0 | 88.0 | 100 | 96.0 |
| 3505 | 100 | 92.9 | 46.4 | 46.4 | 53.6 | 60.7 | 60.7 | 64.3 | 85.7 | 89.3 | 100 |
| 3506 | 100 | 100 | 58.3 | 62.5 | 66.7 | 66.7 | 66.7 | 65.0 | 91.7 | 100 | 100 |
| Mean | 100 | 97.2 | 53.2 | 53.3 | 56.1 | 64.5 | 67.3 | 77.1 | 88.6 | 96.4 | 99.0 |
| SE | 0 | 1.7 | 2.6 | 3.7 | 3.9 | 2.5 | 3.7 | 4.8 | 1.2 | 2.5 | 1.0 |
| | | | | | Left Eye | | | | | | |
| | | | | | P.B.S. | | | | | | |
| 3503 | 100 | 100 | 51.9 | 48.1 | 51.9 | 59.3 | 74.1 | 74.1 | 85.2 | 85.2 | 100 |
| 3504 | 100 | 104.2 | 58.3 | 58.3 | 58.3 | 62.5 | 66.7 | 79.2 | 87.5 | 100 | 100 |
| 3505 | 100 | 100 | 48.1 | 51.9 | 55.6 | 63.0 | 63.0 | 88.9 | 88.9 | 100 | 100 |
| 3506 | 100 | 112.5 | 66.7 | 66.7 | 70.8 | 75.0 | 79.2 | 87.5 | 100 | 108.3 | 100 |
| Mean | 100 | 104.2 | 56.3 | 56.3 | 59.2 | 65.0 | 70.8 | 76.0 | 90.4 | 95.6 | 100 |
| SE | 0 | 2.9 | 4.1 | 4.1 | 4.1 | 3.4 | 3.6 | 5.1 | 3.3 | 5.3 | 0 |

EXAMPLE 4

Figure 4:
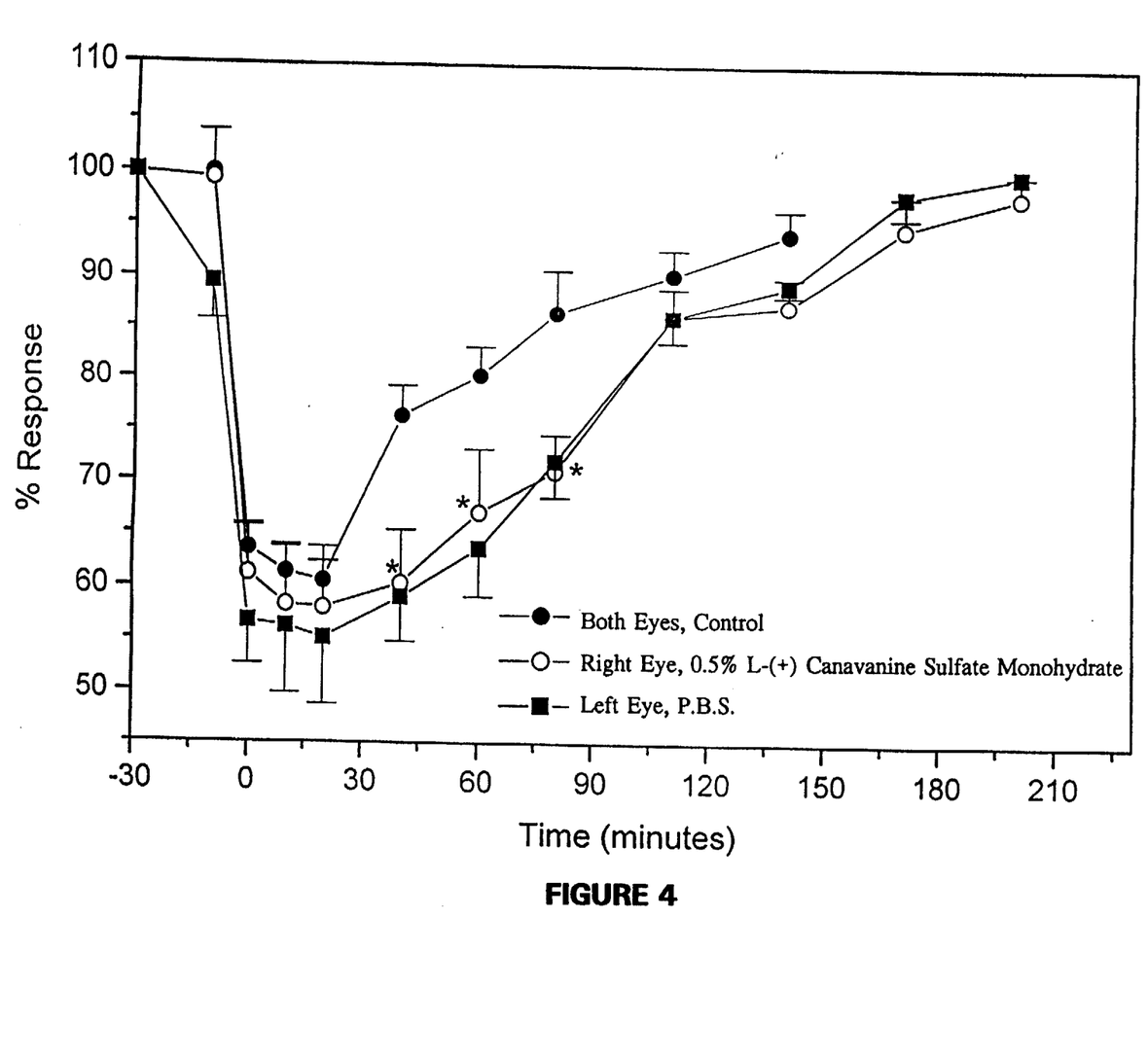
FIG. 4 is a graphical representation of the data of Tables 7 and 8, indicating response of intraocular pressure over time after administration of a 0.5% aqueous solution of L-(+)-canavanine sulfate monohydrate to the right eye of a rabbit. Error bars are indicated for each measurement representing combined results from four rabbits.

The compound L-(+)canavanine was marginally effective in delaying intraocular pressure recovery when tested in accordance with the methods described in Methods and employed in Example 1. As shown in FIG. 4, there was some effect on IOP recovery in the time period between 40 and 80 minutes but little prolonged effect. Data used for the construction of FIG. 4 are tabulated in Tables 7 and 8.

TABLE 7

|         | −10 | 0    | 10   | 20   | 40   | 60   | 80   | 110  | 140  | 170   | 200 |
|---------|-----|------|------|------|------|------|------|------|------|-------|-----|
| ANIMAL  | Control ||||||||||||
| Right Eye |||||||||||||
| 3684    | 100 | 56.5 | 56.5 | 52.2 | 73.9 | 87.0 | 91.3 | 91.3 | 91.3 | 100   | 100 |
| 3685    | 100 | 70.0 | 70.0 | 75.0 | 90.0 | 90.0 | 100  | 100  | 100  | 100   | 100 |
| 3686    | 100 | 54.2 | 54.2 | 54.2 | 66.7 | 70.8 | 70.8 | 91.7 | 87.5 | 87.5  | 100 |
| 3675    | 100 | 70.8 | 66.7 | 66.7 | 79.2 | 75.0 | 75.0 | 87.5 | 100  | 100   | 100 |
| Left Eye |||||||||||||
| 3684    | 100 | 60.9 | 56.5 | 52.2 | 73.9 | 82.6 | 95.7 | 87.0 | 87.0 | 104.3 | 100 |
| 3685    | 100 | 70.0 | 65.0 | 70.0 | 85.0 | 90.0 | 100  | 100  | 100  | 100   | 100 |
| 3686    | 100 | 58.3 | 54.2 | 54.2 | 66.7 | 70.8 | 83.3 | 87.5 | 87.5 | 87.5  | 100 |
| 3675    | 100 | 68.0 | 68.0 | 60.0 | 76.0 | 76.0 | 76.0 | 80.0 | 100  | 100   | 100 |
| Both Eyes |||||||||||||
| Mean    | 100 | 63.6 | 61.4 | 60.6 | 76.4 | 80.3 | 86.5 | 90.6 | 94.2 | 97.4  | 100 |
| SD      | 0   | 6.8  | 6.7  | 8.9  | 8.2  | 8.2  | 11.8 | 6.8  | 6.4  | 6.3   | 0   |
| SB      | 0   | 2.4  | 2.4  | 3.2  | 2.9  | 2.9  | 4.2  | 2.4  | 2.3  | 2.2   | 0   |

TABLE 8

| ANIMAL | −30 | −10 | 0 | 10 | 20 | 40 | 60 | 80 | 110 | 140 | 170 | 210 | 230 |
|--------|-----|-----|---|----|----|----|----|----|-----|-----|-----|-----|-----|
| Right Eye ||||||||||||||
| IOP 0.5% L-(+)-CANAVANINE SULFATE MONOHYDRATE ||||||||||||||
| 3684 | 100 | 87.5 | 66.7 | 54.2 | 58.3 | 54.2 | 62.5 | 70.8 | 83.3 | 83.3 | 87.5 | 91.7 | 91.7 |
| 3685 | 100 | 110.0 | 70.0 | 75.0 | 70.0 | 75.0 | 85.0 | 80.0 | 90.0 | 95.0 | 100 | 100 | |
| 3686 | 100 | 100 | 50.0 | 50.0 | 50.0 | 54.2 | 58.3 | 62.5 | 79.2 | 83.3 | 91.7 | 100 | |
| 3675 | 100 | 100 | 58.3 | 54.2 | 54.2 | 58.3 | 62.5 | 70.8 | 91.7 | 87.5 | 100 | 100 | |
| Mean | 100 | 99.4 | 61.3 | 58.4 | 58.1 | 60.4 | 67.1 | 71.0 | 86.1 | 87.3 | 94.8 | 97.9 | |
| SD | 0 | 9.2 | 9.0 | 11.3 | 8.6 | 9.9 | 12.1 | 7.1 | 5.8 | 5.5 | 6.2 | 4.2 | |
| SE | 0 | 4.6 | 4.5 | 5.6 | 4.3 | 5.0 | 6.1 | 3.6 | 2.9 | 2.8 | 3.1 | 2.1 | |
| T-Value | | | | | | 2.988 | 2.260 | 1.893 | | | | | |
| T 0.05(10) = 1.812 ||||||||||||||
| Left Eye ||||||||||||||
| P.B.S. ||||||||||||||
| 3684 | 100 | 87.0 | 65.2 | 52.2 | 60.9 | 56.5 | 65.2 | 78.3 | 87.0 | 91.3 | 100 | 100 | 100 |
| 3685 | 100 | 95.0 | 60.0 | 75.0 | 70.0 | 70.0 | 75.0 | 75.0 | 90.0 | 90.0 | 100 | 100 | 100 |
| 3686 | 100 | 95.8 | 45.8 | 45.8 | 41.7 | 50.0 | 54.2 | 62.5 | 79.2 | 87.5 | 91.7 | 100 | |
| 3675 | 100 | 80.0 | 56.0 | 52.0 | 48.0 | 60.0 | 60.0 | 72.0 | 88.0 | 88.0 | 100 | 100 | |
| Mean | 100 | 89.5 | 56.8 | 56.3 | 55.2 | 59.1 | 63.6 | 72.0 | 86.1 | 89.2 | 97.9 | 100 | |
| SD | 0 | 7.4 | 8.2 | 12.8 | 12.7 | 8.4 | 8.8 | 6.8 | 4.7 | 1.8 | 4.2 | 0 | |
| SE | 0 | 3.7 | 4.1 | 6.4 | 6.4 | 4.2 | 4.4 | 3.4 | 2.4 | 0.9 | 2.1 | 0 | |

EXAMPLE 5

The procedure for the synthesis of L-arginine ethyl ester or $N_\alpha$-benzoyl-L-arginine ethyl ester is also applicable to the synthesis of other esters, including isopropyl, isobutyryl, t-butyryl, valeryl, isovaleryl, benzyl and di- and triesters of L-arginine or its $N_\alpha$-benzoyl derivatives with ethylene glycol and glycerol respectively.

Synthesis of $N_\alpha$-benzoyl-L-arginine ethyl ester hydrochloride $N_\alpha$-benzoyl-L-arginine was obtained from MTM Research Chemicals, Lancaster Synthesis, Inc., Windham, N.H. The $N_\alpha$-benzoyl-L-arginine, 0.4 g, was placed in a two-necked round bottom flask equipped with a stirring bar and suspended in an excess (~5 ml) of ethyl alcohol. The outlet from the flask was attached to a mineral oil bubbler and dry hydrogen chloride gas was bubbled via the inlet into the stirred solution to the point of saturation; a mildly exothermic reaction ensued with gradual dissolution of the suspended starting material. The reaction was monitored by thin layer chromatography (TLC) in solvent system (dichloromethane:methanol: 80:20; v/v) until no starting material was left.

Upon completion of the reaction, the excess ethyl alcohol was removed on a rotary evaporator under reduced pressure to afford the crystalline white solid; it was found identical with an authentic specimen (Sigma Chemical Company, St. Louis, Mo.).

Synthesis of $N_\alpha$-benzoyl-L-arginine-benzyl ester hydrochloride

A method similar to the preparation of $N_\alpha$-benzoyl-L-arginine benzyl ester was employed except that the starting reaction mixture was $N_\alpha$-benzoyl-L-arginine and benzyl alcohol. The reaction mixture was stirred and treated with dry HCL. The final purification step included flash column chromatography on silica gel (230–400 mesh size). Elution with pure dichloromethane/methanol (95:5; v/v). FTIR (neat film): 3330 (NH and $NH_2$), 1739, 1732 (C=O) , 1666, 1660, 1650, 1643, 1633, 1577, 1536, 1490,1454,1213, 1187 and 1158 $cm^{-1}$. $^1H$ NMR ($D_2O$): δ7.87–7.38(m,10H), 5.21(br s, 1H), 4.7(br s 2H), 4.5(br s, 1H), 3.2(m, 2H), 2.0–1.6 (m, 4H); $^{13}C$ NMR ($D_2O$): δ172,63, 169.94 (C=O), 157.21 (guanidino-C), 140,9, 135.51, 133.48, 132.04, 128.65, 128.56, 128.42, 128.38, 127.89, 127.37, 126.96 (aromatic Cs), 67.41 (benzyl-CH2), 40.78, 28.08, 27.96 and 24.54.

Synthesis of Di-(N$_\alpha$-benzoyl-L-argininyl)ethylene hydrochloride

The ethylene glycol ester of di-N$_\alpha$-benzoyl-L-arginine was prepared by a method similar to that employed for the preparation of the ethyl and benzyl esters except that the starting mixture was N$_\alpha$L-benzoyl-L-arginine and ethylene glycol. The reaction mixture was stirred and treated with dry HCl. Ethylene glycol was removed by flash column chromatography on silica gel (230-400 mesh size). The pure product, a glassy hygroscopic solid, was obtained by elution of the column with dichloromethane-methanol (90:10; v/v). FTIR (neat film): 3332 (NH and NH$_2$), 1737 (C=O), 1644, 1578. 1537. 1489. 1190 and 1076 cm$^{-1}$. $^1$H NMR (D$_2$O) $\delta$7.79-7.50 (m, 10H), 4.74-4.50 (m, 6H), 3.22 (m, 4H), 2.1-1.68 (m, 8H); $^{13}$C NMR(D$_2$O): $\delta$173.74, 170.30 (C=O), 157.05 (guanidino-C), 133.30, 132.21, 127.03 (aromatic carbons), 52.92, 52.84, 40,67, 27.87 and 24.47. The structure of the product is shown in FIG. 5.

Synthesis of Tri-(N$_\alpha$-benzoyl-L-argininyl)glycerol hydrochloride

A method similar to that employed for the preparation of the ethyl, benzyl and ethylene glycol esters had a starting mixture of N$_\alpha$-L-benzoyl-L-arginine and glycerol. The reaction mixture was stirred and treated with dry HCl. The final purification was accomplished by flash column chromatography on silica gel (230-400 mesh size). The structure of the product is shown in FIG. 5.

Alternatively, esters may be obtained employing thionyl chloride in place of anhydrous hydrogen chloride gas in the above procedures.

Other procedures eliminate or minimize racemization during the esterification process. This involves the reaction of L-arginine or its N$_\alpha$-protected derivative in methylene chloride mixed with dicyclohexylcarbodiimide (DCC) or its water soluble form, 1-ethyl-3-[3-(dimethylamino)propyl]carbodiimide hydrochloride, under cold conditions (ice bath) in the presence of 4-(dimethylamino)pyridine.

REFERENCES

The references listed below are incorporated herein to the extent that they supplement, explain, provide a background for or teach methodology, techniques and-/or compositions employed herein.

Bodor, N. and Visor, G., *Exp. Eye Res.*, vol. 38, 621-626 (1984).

Bredt, D. S. and Snyder, S. H., Proc. Natl. Acado Sci, 87, 682-685 (1990)

Chiou, G. C. Y. and Li, B. H. P., *J. Ocular Pharmacol.*, vol. 8(1), 11-21 (1992)

"Drug Carrier Systems" F. H. D Roerdink and A. M. Kroon Eds., by Hoes, C. J. T. and Feijen, J. in "The Application of Drug-Polymer conjugates in Chemotherapy", Wiley and Sons, New York, 1989.

Greco, A. V., Ricci, B., Altomonte, L., Rebuzzi, A., Manna, R. and Ghirlanda, G., *Ophthalmologica*, Vol. 179, pp. 168-172 (1979).

Kilbourne, et al., WO 90/04024, Apr. 4, 1991.

Lee, V. H., *J. Cont. Release*, vol. 11, 79-90 (1990).

Lee, V. H. and Li, V. H. K., *Adv. Drug Deliv. Rev.* vol. 3, 1-38 (1989)

Ludwig, A. and Ooteghem, M. V., Int. *J. Pharmaceutics*, vol. 54, 95-102 (1989).

Myers, P. R., Minor, R. L., Jr., Guerra, R., Jr., Bates, J. N. and Harrison, D. G., *Nature* 345, 161-164 (1990).

Nathanson, J. A., *The Journal of Pharmacology and Experimental Therapeutics*, Vol. 260, pp. 956-960 (1992).

Radomski, M. W., Rees, D. D., Dutra, A. and Moncada, S., *Br. J. Pharmacol.* 107, 745-749 (1992).

"Remington's Pharmaceutical Sciences" 15th Edition (Mack Publishing Co., Easton, Pa.).

Rubanyi et al., *Journal of Cardiovascular Pharmacology*, Vol. 17, pp. S41-S45 (1991)

Venturini, C. M., Knowles, R. G., Palmer, R. M. J. and Moncada, S., *Biochem. Biophys. Res. Commun.* 180, 920-925 (1991).

What is claimed is:

1. A method of reducing intraocular pressure, comprising administering to a subject experiencing excess intraocular pressure an effective amount of an L-arginine ester selected from a group consisting of compounds having the formula:

where R' is H, COC$_6$H$_5$, C$_6$H$_5$ CH$_2$OCO—, COCH$_3$ or (CH$_3$)$_3$OCO; R is selected from a group consisting of NH$_2$ and NHR" where R" is lower alkyl or aryl; COH(CH$_3$)$_2$, OC(CH$_3$)$_3$, OCH$_2$C$_6$H$_5$, OH and OR''' where R''' is lower alkyl; and pharmaceutically acceptable salts thereof.

2. The method of claim 1 wherein the L-arginine ester is selected from a group consisting essentially of N$_\alpha$-benzyloxycarbonyl-L-arginine derivatives having a formula;

were R is selected from a group consisting of NH$_2$ and NHR" where R" is lower alkyl or aryl; OCH(CH$_3$)$_2$, OC(CH$_3$)$_3$, OCH$_2$C$_6$H$_5$, OH and OR'''where R''' is lower alkyl; and pharmaceutically acceptable salts thereof.

3. The method of claim 2 wherein the L-arginine ester is N$_\alpha$-benzoyl-L-arginine ethyl ester.

4. The method of claim 1 or claim 2 wherein said L-arginine ester derivative is administered topically to the eye in a pharmaceutically acceptable vehicle.

5. The method of claim 1 wherein the L-arginine ester is L-(+)canavanine.

6. The method of claim 1 wherein the effective amount is between about 0.01-5% by weight of the composition.

7. The method of claim 1 wherein the effective amount is between about 0.1-0.5% by weight of the composition.

8. The method of claim 1 wherein said L-arginine ester is administered from 1 to 8 times daily.

9. The method of claim 1 wherein said L-arginine ester is administered 2 to 4 times daily.

10. A method of treating glaucoma, comprising administering to a subject suspected of having glaucoma an effective amount of a pharmaceutically acceptable composition comprising $N_\alpha$-benzoyl-L-arginine ethyl ester or L-(+)canavanine.

11. A method of treating glaucoma, comprising administering to a subject suspected of having ischemic retinopathy an effective amount of a pharmaceutically acceptable composition comprising $N_\alpha$-benzoyl-L-arginine ethyl ester or L-(+)canavanine.

12. A method of reducing intraocular pressure, comprising administering to a subject experiencing excessive intraocular pressure an effective amount of a pharmaceutically acceptable solution consisting essentially of L-arginine.

* * * * *

UNITED STATES PATENT AND TRADEMARK OFFICE
CERTIFICATE OF CORRECTION

PATENT NO. : 5,364,884

DATED : November 15, 1994

INVENTOR(S) : Rajender S. Varma and George C. Y. Chiou

It is certified that error appears in the above-indentified patent and that said Letters Patent is hereby corrected as shown below:

```
On the title page, item [73] Assignee: insert
--; and Texas A&M University System, College Station, Tex.--
```

Signed and Sealed this

Sixteenth Day of May, 1995

Attest:

BRUCE LEHMAN

Attesting Officer

Commissioner of Patents and Trademarks